United States Patent [19]

Shima et al.

[11] Patent Number: 4,767,874

[45] Date of Patent: Aug. 30, 1988

[54] STABLE FREEZE-DRIED PREPARATIONS OF AN ANTICANCER PLATINUM COMPLEX

[75] Inventors: Kazuhiro Shima, Osaka; Takayuki Tsukada, Hyogo; Hirotane Kagawa, Osaka, all of Japan

[73] Assignee: Shionogi & Co., Ltd., Osaka, Japan

[21] Appl. No.: 905,456

[22] Filed: Sep. 10, 1986

[30] Foreign Application Priority Data

Sep. 25, 1985 [JP] Japan .................................. 60-213180

[51] Int. Cl.$^4$ .............................................. C07F 15/00
[52] U.S. Cl. ...................................................... 556/137
[58] Field of Search ........................................... 556/137

[56] References Cited

U.S. PATENT DOCUMENTS

| 4,083,969 | 4/1978 | Inoue et al. | 424/182 |
| 4,315,002 | 2/1982 | Maurer | 424/181 |
| 4,575,550 | 3/1986 | Totani | 556/137 X |
| 4,577,038 | 3/1986 | Totani et al. | 556/137 |
| 4,598,091 | 7/1986 | Schonenberger et al. | 514/492 |
| 4,658,048 | 4/1987 | Totani et al. | 556/137 |

FOREIGN PATENT DOCUMENTS

| 0021009 | 1/1981 | European Pat. Off. | 556/137 UX |
| 0057023 | 8/1982 | European Pat. Off. | 556/137 UX |
| 0181166 | 5/1986 | European Pat. Off. | 556/137 UX |
| 2306702 | 11/1976 | France | 556/137 UX |
| 2127291 | 4/1984 | United Kingdom | 556/137 UX |

*Primary Examiner*—Paul F. Shaver
*Attorney, Agent, or Firm*—Wenderoth, Lind & Ponack

[57] ABSTRACT

Stable freeze-dried preparations of an anticancer platinum complex, i.e. glycolato-cis-diammineplatinum (II), containing at least one member selected from the group consisting of glucan, water-soluble vinyl polymer, and polyethylene glycol as stabilizers, are very useful in the treatment of various cancers.

11 Claims, No Drawings

STABLE FREEZE-DRIED PREPARATIONS OF AN ANTICANCER PLATINUM COMPLEX

BACKGROUND OF INVENTION

1. Field of Invention

This invention relates to pharmaceutical preparations of glycolato-cis-diammineplatinum (II) (hereinafter sometimes referred to as the platinum compound) of the following formula:

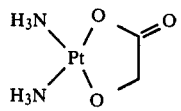

which comprises at least one member selected from the group consisting of glucan, water-soluble vinyl polymer and polyethylene glycol as stabilizers.

2. Prior Arts

Cisplatin is one of the already-marketed cis-platinum compounds. Stable cisplatin compositions were disclosed in JPN Unexamined Patent Publication Nos. 54-157817 and 56-152415 and a method to stabilize cisplatin by adding sodium chloride, mannitol and variable-amount of alcohol was disclosed in JPN Unexam. Pat. Pub. No. 59-78117.

SUMMARY OF THE INVENTION

Glycolato-cis-diammineplatinum (II) is very effective in the treatment of various cancers but is unstable under usual storage conditions. This invention provides stable freeze-dried preparations of said anticancer complex containing at least one member selected from the group consisting of glucan, water-soluble vinyl polymer, and polyethylene glycol as stabilizers.

DESCRIPTION OF PREFERRED EMBODIMENT

1. Problem to be Solved

The platinum compound in this invention is a highly safe compound with a potent anticancer action, as disclosed in JPN Unexam. Pat. Pub. No. 59-222497. However, when formulated into freeze-dried preparations for injection or for preservation by an ordinary method, the platinum compound is so unstable as to turn gray or brown in a comparatively short period of time during long-term storage or under accelerated conditions. Decrease in the activity or change in color is observed even if the preparation is in a form of solution or powder filled in vials.

Therefore, the compound untreated has been deemed relatively low in commercial value since it has been hard to manufacture, by a conventional method, preparations of the platinum compound preservable for a long period of time at room temperature.

2. Means to Solve the Problem

The present inventors have discovered that some water-soluble polymers are effective in stabilizing the platinum compound; the present invention is based on this findings.

The water-soluble polymers in this invention are glucan known as natural polysaccharide or synthetic polymers. The glucan which may be used in this invention includes, for example, water-soluble neutral glucans such as dextran, pullulan, amylose, and the like; water-soluble modified starches or its derivatives such as dextrin, optionally methylated α-, β-, or γ-cyclodextrin, soluble starch, hydroxyethyl starch, and the like; water-soluble cellulose derivatives such as methyl cellulose (MC), hydroxyethyl cellulose (HEC), hydroxypropyl cellulose (HPC), hydroxypropylmethyl cellulose (HPMC), carboxymethyl cellulose sodium salt (CMC-Na), and the like.

The synthetic polymers include, for example, water-soluble vinyl polymers such as polyvinyl alcohol (PVA), polyvinylpyrrolidone (PVP), and the like; the polyethylene glycol (PEG) having mean molecular weight ranging 1500–9000; and the like.

All of these stabilizers may be used to attain the purpose of this invention. Dextran, cyclodextrin, and pullulan are preferable in view of the fact that the compositions of this invention are used in intravenous injection. Amongst all, dextran having mean molecular weight ranging 40,000 to 70,000 is most preferably used.

Saccharides or sugar alcohols may be, if desired, added thereto as well-known excipients, fillers, and tonicity agents.

Addition of these stabilizers is effective in preventing coloration of the platinum compound. There is no upper limit in the ratio of addition of these stabilizers to the platinum compound for attaining the purpose of this invention. But it is not desirable to use an excessive amount of additives in the case of pharmaceutical products. Taking into account the operability in distributing the composition into containers and the viscosity of the reconstituted solution, the stabilizers should be used at a ratio of 0.05–5, preferably 0.1–3, and more preferably 0.3–1 weight-parts to 1 weight-part of the platinum compound. Addition of the stabilizers at a ratio below the lower limit as defined above is insufficient to prevent the change in color.

Therefore, in order to prepare a stable freeze-dried preparation of said platinum compound, it is appropriate to make a solution of the platinum compound and stabilizers dissolved in an aqueous solvent, then to freeze-dry it by a conventional method. Physical mixture of the platinum compound with stabilizers is less effective in the stabilization of the preparation.

Ordinarily, the freeze-drying is achieved by means of a tray freeze-drying method, spray freeze-drying method, vial freeze-drying method, etc., that is, the aforementioned mixture is cooled, frozen, and then the moisture of the frozen product is sublimed under a high vacuum to give the objective freeze-dried preparation. For instance, vials containing the aqueous mixture so prepared are placed in a freeze-drier for 5 to 72 hours, during the course of which the shelf-temperature is lowered between about $-80°$ C. and $-20°$ C., then raised and kept below about $-3°$ C., more preferably below about $-10°$ C. under a pressure of 0.005 to 1 mb, to give a freeze-dried preparation.

As is widely known, the platinum compound is soluble in water and the preparation produced under sterile conditions can be used for intravenous injection and is also suitable as a long-term preservation form of bulk products. Preparations produced under sterile conditions can be dissolved in distilled water for injection, transfusion, etc. and intravenously administrated.

This invention is explained in more detail by the following Examples, which are not intended to limit the scope of this invention.

GENERAL PROCEDURE

A solution of glycolato-cis-diammineplatinum (II) (A mg) and stabilizer (B mg; in dry weight) dissolved in 1 ml of distilled water for injection is filtered through a 0.22 μm pore membrane filter to give a sterile solution, which is then distributed into vials in a prefixed amount to each. The vials are placed in a freeze-drier, cooled to about −40° C. and kept at the same temperature for about 3 hours. Then, after the temperature is elevated up to about −10° C. or below, practically entire amount of the water is removed by sublimation under pressure of about 0.1 mb. After completion of the sublimation, the vials are warmed up to about 40° C. and kept for 4 hours to give a freeze-dried preparation.

EXAMPLE 1

A solution of 10 mg of glycolato-cis-diammineplatinum (II) and 5 mg (in dry weight) of dextran 70 dissolved in 1 ml of distilled water for injection is filtered through a 0.22 μm pore membrane filter to give a sterile solution, 5 ml each of which is distributed into 14 ml vials.

The vials are placed in a freeze-drier, cooled rapidly to about −40° C. and kept at the same temperature for further 1 hour after the frozen aqueous layer (product temperaure) is cooled down to −35° C. or below. Then the temperature is elevated up to about −10° C. or below, and the moisture is sublimed under pressure of about 0.1 mb. After completion of the sublimation, the vials are warmed up to about 40° C. and kept for 4 hours to give a freeze-dried preparation. The preparation contains 50 mg of glycolato-cis-diammineplatinum (II) per vial.

EXAMPLES 2-21

The following freeze-dried preparations (Table 1) were obtained according to the general procedure.

The respective filtrates (1 ml each) are distributed into 3 ml vials to give freeze-dried preparations containing 10 mg of glycolato-cis-diammineplatinum (II) per vial.

TABLE 1

| Exam. No. | Stabilizer (B mg) | Pt compd. (A mg) |
|---|---|---|
| 2 | Dextran 40 (0.5) | 10 |
| 3 | Dextran 40 (1.0) | 10 |
| 4 | Dextran 40 (10.0) | 10 |
| 5 | Dextran 70 (1.0) | 10 |
| 6 | Dextran 70 (0.5) | 10 |
| 7 | Dextran 70 (1.0) | 10 |
| 8 | Dextran 70 (10.0) | 10 |
| 9 | Dextran 70 (40.0) | 10 |
| 10 | Dextran (mol. wt. 100,000-200,000) (10.0) | 10 |
| 11 | α-Cyclodextrin (10.0) | 10 |
| 12 | β-Cyclodextrin (10.0) | 10 |
| 13 | Dextrin (10.0) | 10 |
| 14 | Pullulan (PF-20) (10.0) | 10 |
| 15 | MC (15 cps) (10.0) | 10 |
| 16 | HPC (SL) (10.0) | 10 |
| 17 | HPMC (2906) (10.0) | 10 |
| 18 | CMC-Na (10 cps) (10.0) | 10 |
| 19 | PVA (PA-20) (10.0) | 10 |
| 20 | PVP (K-90) (10.0) | 10 |
| 21 | PEG (6000) (10.0) | 10 |

EXPERIMENT 1

Effect for preventing changes in color was observed on both powders and solutions just after reconstituted of the preparations manufactured in Examples 1 to 21 (Table 2). The reconstituted solutions were so prepared that the final concentration of said platinum compound reached 1% (w/v). The degrees of coloration changes are shown as (−) to (+++) in the Table. In the same manner as above, the reference compositions 1 and 2 were also observed for comparison. The composition numbers shown below correspond to the Example numbers.

NOTE 1

Reference composition 1: A physical mixture of dextran 70 (1 weight-part) with the platinum compound (1 weight-part).

Reference composition 2: A freeze-dried preparation of platinum compound containing no stabilizers.

NOTE 2

(−) indicates no change in color was observed, (±) a slight change in color observed, and (+) to (+++) indicate changes in color were getting stronger in the order given.

TABLE 2

| Compo- sition Tested | Appearance (after a 10 day storage at 60° C.) | |
|---|---|---|
| | Powder | Solution Reconstituted |
| 1 | White (−) | Colorless, Transparent (−) |
| 2 | White (±) | Colorless, Transparent (±) |
| 3 | White (−) | Colorless, Transparent (−) |
| 4 | White (−) | Colorless, Transparent (−) |
| 5 | Gray (+) | Red Purple Transparent (+) |
| 6 | White (±) | Colorless, Transparent (±) |
| 7 | White (−) | Colorless, Transparent (−) |
| 8 | White (−) | Colorless, Transparent (−) |
| 9 | White (−) | Colorless, Transparent (−) |
| 10 | White (−) | Colorless, Transparent (−) |
| 11 | White (−) | Colorless, Transparent (−) |
| 12 | White (−) | Colorless, Transparent (−) |
| 13 | White (−) | Colorless, Transparent (−) |
| 14 | White (−) | Colorless, Transparent (−) |
| 15 | White (−) | Colorless, Transparent (−) |
| 16 | Grayish brown (+) | Reddish Brown, Transparent (++) |
| 17 | Grayish brown (+) | Reddish Brown, Transparent (++) |
| 18 | White (−) | Colorless, Transparent (−) |
| 19 | White (−) | Colorless, Transparent (−) |
| 20 | White (−) | Colorless, Transparent (−) |
| 21 | Gray (++) | Red Purple, Transparent (+) |
| Ref. 1 | Gray (++) | Reddish Brown, Transparent (+++) |
| Ref. 2 | Grayish brown (+++) | Reddish Brown, Transparent (+++) |

EXPERIMENT 2

The following compositions were examined with respect to decrease in the potency of the platinum compound (Table 3). Table 3 shows the remaining potency in each composition in percent and changes in color by (−) to (+++).

TABLE 3

| | 40° C. | | |
|---|---|---|---|
| Composition | 1 month after | 2 month after | 4 month after |
| 1 | 100.8 (−) | 99.2 (−) | 101.1 (−) |
| 8 | 100.4 (−) | 97.1 (−) | 98.4 (−) |
| 9 | 100.0 (−) | 98.6 (−) | 99.7 (−) |
| Ref. 1 | 99.5 (++) | 99.4 (++) | — |

What is claimed is:

1. A freeze-dried preparation of glycolato-cis-diammineplatinum (II) as the active ingredient containing at least one member selected from the group consisting of glucan, water-soluble vinyl polymer, and polyethylene glycol as a stabilizer.

2. A freeze-dried preparation claimed in claim 1 wherein the glucan is water-soluble neutral glucan.

3. A freeze-dried preparation claimed in claim 1 wherein the glucan is water-soluble modified starch or its derivative.

4. A freeze-dried preparation claimed in claim 1 wherein the glucan is water-soluble cellulose derivative.

5. A freeze-dried preparation claimed in claim 2 wherein the water-soluble neutral glucan is dextran, pullulan, or amylose.

6. A freeze-dried preparation claimed in claim 2 wherein the water-soluble neutral glucan is dextran.

7. A freeze-dried preparation claimed in claim 3 wherein the water-soluble modified starch or its derivative is dextrin, cyclodextrin, soluble starch, or hydroxyethyl starch.

8. A freeze-dried preparation claimed in claim 4 wherein the water-soluble cellulose derivative is methyl cellulose, hydroxyethyl cellulose, hydroxypropyl methyl cellulose, or carboxymethyl cellulose sodium salt.

9. A freeze-dried preparation claimed in claim 1 wherein the water-soluble vinyl polymer is polyvinyl alcohol or polyvinyl pyrrolidone.

10. A freeze-dried preparation claimed in claim 1 which contains the stabilizer at a ratio of 0.05–5 weight-parts to 1 weight-part of said active ingredient.

11. A freeze-dried preparation claimed in claim 1 which contains the stabilizer at a ratio of 0.1–3 weight-parts to 1 weight-part of said active ingredient.

* * * * *